(12) United States Patent
Schreiber et al.

(10) Patent No.: US 7,173,015 B2
(45) Date of Patent: Feb. 6, 2007

(54) INHIBITION OF SYK KINASE EXPRESSION

(75) Inventors: Alan D Schreiber, Philadelphia, PA (US); Zena Indik, Philadelphia, PA (US); Moo-Kyung Kim, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 10/880,612

(22) Filed: Jul. 1, 2004

(65) Prior Publication Data

US 2005/0075306 A1   Apr. 7, 2005

Related U.S. Application Data

(60) Provisional application No. 60/484,299, filed on Jul. 3, 2003.

(51) Int. Cl.
*A61K 48/00* (2006.01)
*C07H 21/02* (2006.01)
*C07H 21/04* (2006.01)
*C12Q 1/68* (2006.01)
*C12N 15/85* (2006.01)

(52) U.S. Cl. .......................... 514/44; 435/6; 435/91.1; 435/325; 435/375; 536/23.1; 536/24.5

(58) Field of Classification Search .............. 435/91.1, 435/91.3, 325, 375; 514/44
See application file for complete search history.

(56) References Cited

U.S. PATENT DOCUMENTS

| | | | |
|---|---|---|---|
| 6,242,427 B1 * | 6/2001 | Schreiber et al. ............ 514/44 |
| 2003/0232364 A1 | 12/2003 | Shaughnessy et al. |
| 2004/0009523 A1 | 1/2004 | Shaughnessy et al. |
| 2004/0018522 A1 | 1/2004 | Dangond et al. |
| 2004/0028685 A1 | 2/2004 | Kinch et al. |
| 2004/0106156 A1 | 6/2004 | Perez et al. |
| 2004/0219575 A1 | 11/2004 | Neuman et al. |
| 2005/0112630 A1 | 5/2005 | Shaughnessy et al. |
| 2005/0130117 A1 | 6/2005 | Davis et al. |
| 2005/0147593 A1 | 7/2005 | Kinch |
| 2005/0153425 A1 | 7/2005 | Xu et al. |
| 2005/0153923 A1 | 7/2005 | Kinch |
| 2005/0245475 A1 | 11/2005 | Khvorova et al. |
| 2005/0246794 A1 | 11/2005 | Khvorova et al. |
| 2005/0267059 A1 | 12/2005 | Beardsley et al. |
| 2006/0003322 A1 | 1/2006 | Bentwich |
| 2006/0058255 A1 | 3/2006 | Chen et al. |
| 2006/0073474 A1 | 4/2006 | Perez et al. |
| 2006/0127385 A1 | 6/2006 | Sarkar et al. |
| 2006/0141493 A1 | 6/2006 | West et al. |
| 2006/0150262 A1 | 7/2006 | Bienkowska et al. |

FOREIGN PATENT DOCUMENTS

WO   WO 02/44321   *   6/2002

OTHER PUBLICATIONS

Stenton et al. Aeroxlized Syk Antisense Suppresses Syk Expression, Mediator Release from Macrophages, and Pulmonary Inflammation. J. Immunology 2ooo: vol. 164: 3790-3797. The American Association of Immunologists.*

Hammond et al. Post-Transcriptional Gene Silencing by Double-Stranded RNA. Nature 2001, vol. 2: 110-119. MacMillan Magazines Ltd.*

Takada and Aggarwal, "TNF, Activates Syk Protein Tyrosine Kinase Leading TNF-Induced MAPK Activation, NF-κB Activation, and Apoptosis", The Journal of Immunology 173: 1066-1077 (2004).

Takada et al, "Hydrogen Peroxide Activates NF-κB through Tyrosine Phosphorylation of IκBα and Serine Phosphorylation of p65", The Journal of Biological Chemistry 278(26):24233-24241 (2003).

Ulanova et al, "Syk tyrosine kinase participates in $\beta_1$-integrin signaling and inflammatory responses in airway epithelial cells", Am. J. Physiol. Lung Cell Mol. Physiol. 288:L497-L-507 (2005).

Stenton et al, "Inhibition of Allergic Inflammation in the Airways Using Aerosolized Antisense to Syk Kinase", The Journal of Immunology 169:1028-1036 (2002).

Mammalian Gene Collection (MGC) Program Team, Contributed by Francis S. Collins, "Generation and initial analysis of more than 15,000 full-length human and mouse cDNA sequences", PNAS 99(26):16899-16903 (2002).

Rowley et al, "Molecular Cloning of Roden $p72^{Syk}$", The Journal of Biological Chemistry 270(21):12659-12664 (1995).

Law et al, "Molecular Cloning of Human Syk", The Journal of Biological Chemistry 269(16):12310-12319 (1994).

Vickers et al, "Efficient Reduction of Target RNAs by Small Interfering RNA and RNase H-dependent Antisense Agents", The Journal of Biological Chemistry 278(9):7108-7118 (2003).

Scherer and Rossi, "Approaches for the sequence-specific knockdown of mRNA", Nature Biotechnology 21(12):1457-1465 (2003).

Kalota et al, "Progress in the Development of Nucleic Acid Therapeutics for Cancer", Cancer Biology & Therapy 3(1):4-12 (2004).

Holen et al, "Positional effects of short interfering RNAs targeting the human coagulation trigger Tissue Factor", Nucleic Acids Research 30(8):1757-1766 (2002).

Jarad et al, "Nucleic acid-based techniques for post-transcriptional regulation of molecular targets", Current Opinion in Nephrology and Hypertension 12:415-421 (2003).

Patil et al, "DNA-based Therapeutics and DNA Delivery Systems: A Comprehensive Review", The AAPS Journal 7(1) Article 9:E-61-E77 (2005).

Hu et al, "Relative gene-silencing efficiencies of small interfering RNAs targeting sense and antisense transcripts from the same genetic locus", Nucleic Acids Research 32(15):4609-4617 (2004).

* cited by examiner

*Primary Examiner*—Sean McGarry
*Assistant Examiner*—Kimberly Chong
(74) *Attorney, Agent, or Firm*—Nile & Vanderhye P.C.

(57) ABSTRACT

The present invention relates, in general, to Syk kinase and, in particular, to a method of inhibiting Syk kinase expression using small interfering RNA (siRNA).

14 Claims, 8 Drawing Sheets siRNA-1    5' Human, bp 296 to bp 316; Mouse and Rat, bp 307 to bp 327

Targeted region (cDNA):    5'    aagaagcccttcaaccggccc

Sense siRNA            5'-        gaagcccuucaaccggccc        UU 3'
Antisense siRNA        3'-UU      cuucgggaaguuggccggg             5' siRNA-2:  Human, bp 364 to bp 382; Mouse and Rat, bp 375 to bp 393

Targeted region (cDNA)    5'    aacctcatcagggaatatgtg sense              5'-     ccucaucagggaauaugug     UU 3'
antisense        3'-UU     ggaguagucccuuauacac          5'

Figure 1.

Syk

Actin

Western blot analysis: Syk protein expression in HS-24 cells

Cont siRNA -1 siRNA -2
24 hr 48 hr 24 hr 48 hr

Densitometry Units

| | | |
|---|---|---|
| Control | | 136288 |
| si RNA -1 | 24hrs | 134979 |
| si RNA -1 | 48hrs | 147055 |
| si RNA -2 | 24hrs | 146516 |
| si RNA -2 | 48hrs | 61808 (45% of control) |

Figure 4

Figure 5
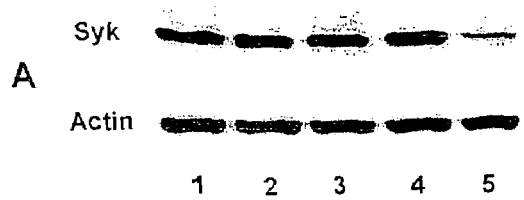
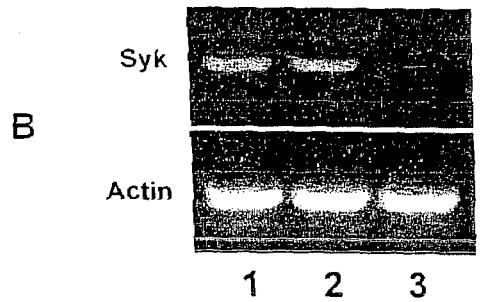
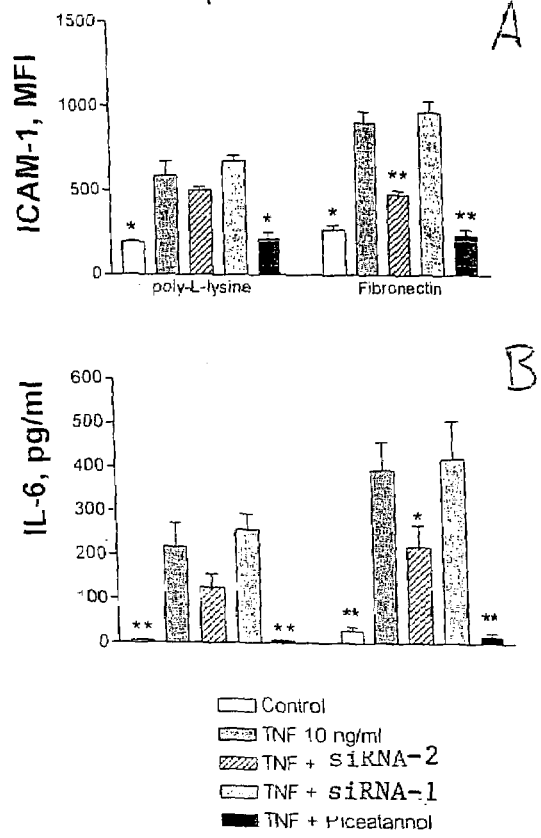
Figure 6

INHIBITION OF SYK KINASE EXPRESSION

This application claims priority from Provisional Application No. 60/484,299, filed Jul. 3, 2003, the entire contents of which are incorporated herein by reference.

TECHNICAL FIELD

The present invention relates, in general, to Syk kinase and, in particular, to a method of inhibiting Syk kinase expression using small interfering RNA (siRNA).

BACKGROUND

Double stranded RNA has been shown to be a powerful agent for interfering with gene expression in a number of organisms, including *C. elegans* and *Drosophila*, as well as plants (Bernstein et al, RNA 7:1509–2151 (2001), McManus et al, Nat. Rev. Genet. 3:737–747 (2992), Hutvagner et al, Curr. Opin. Genet. Dev. 12:225–232 (2002), Zamore, Nat. Struct. Biol. 8:746–750 (2001) Tuschl et al, Genes Dev. 13:3191–3197 (1999)). Early problems in silencing mammalian genes with double stranded RNA arose because the mammalian immune system destroys cells that contain double stranded RNA, through mechanisms such as the interferon response, evolved as defense against invading RNA viruses (Clarke et al, RNA 1:7–20 (1995)). It has been demonstrated, however, that very short RNA fragments (e.g., 20–23 nt in length), designated small interfering RNA (siRNA), are able to escape the immune response. Thus introduced siRNAs can function well as gene silencing agents in mammalian cells (Elbashir et al, Nature 411: 494–498 (2001), Elbashir et al, Genes Dev. 15:188–200 (2001), Paddison et al, Genes Dev. 16:948–958 (2002), Wianny et al, Nat. Cell Biol. 2:70–75 (2000)).

As it is presently understood, RNAi involves a multi-step process. Double stranded RNAs are cleaved by the endonuclease Dicer to generate 21–23 nucleotide fragments (siRNA). The siRNA duplex is resolved into 2 single stranded RNAs, one strand being incorporated into a protein-containing complex where it functions as guide RNA to direct cleavage of the target RNA (Schwarz et al, Mol. Cell. 10:537–548 (2002), Zamore et al, Cell 101:25–33 (2000)), thus silencing a specific genetic message (see also Zeng et al, Proc. Natl. Acad. Sci. 100:9779 (2003)).

Anti-sense DNA has also been widely used to inhibit gene expression (Roth et al, Annu. Rev. Biomed. Eng. 1:265–297 (1999)). Once inside the cell, anti-sense oligonucleotides (ASO) recognize, then bind tightly to complementary mRNA, thus preventing the mRNA from interacting with the protein translation machinery of the cell.

It has been demonstrated that inhibition of Syk kinase expression by Syk kinase mRNA ASO dramatically diminishes Fcγ receptor signaling (Matsuda et al, Molec. Biol. of the Cell 7:1095–1106 (1996)), and that Syk kinase mRNA ASO introduced by aerosol into rat lungs protects against Fcγ receptor-induced lung inflammation (Stenton et al, J. Immunol. 169:1028–1036 (2002)).

At least in certain systems, siRNA is more potent and reliable than ASO as an inhibitor of gene expression. The present invention results from studies designed to test the efficacy of siRNA as an inhibitor of Syk kinase expression.

SUMMARY OF THE INVENTION

The present invention relates generally to Syk kinase. In a preferred embodiment, the invention relates to a method of inhibiting Syk kinase expression using small interfering RNA (siRNA) and to therapeutic strategies based on such a method.

Objects and advantages of the present invention will be clear from the description that follows.

BRIEF DESCRIPTION OF THE DRAWINGS

FIG. 1. The sense strand of each Syk kinase siRNA is the same sequence as the target sequence with the exception of the initial template adenine dimer and terminal overhang uridine dimer. The antisense strand of the siRNA is the reverse complement of the target sequence. The polynucleotide sequences are shown in SEQ ID NOS 27, 23–24, 28 and 25–26, respectively, in order of appearance.

FIG. 4. Western blot analysis: Syk protein expression in HS-24 cells.

FIGS. 5A and 5B. (FIG. 5A) HS-24 cells, following siRNA treatment, were lysed and equal amounts of total protein in HS-24 cell lysates were resolved by 10% SDS gel electrophoresis, and analyzed by Western blot using monoclonal antibody to Syk or actin. Lane 1—no treatment, lane 2—siRNA-1 (control) 24 h treatment, lane 3—siRNA-1 48 h treatment, lane 4—siRNA-2 24 h treatment, lane 5—siRNA-2 48 h treatment. (FIG. 5B) RNA was isolated and RT-PCR was performed for Syk and β-actin. Lane 1—no treatment, lane 2—SiRNA-1 (control) 48 h treatment, lane 3—siRNA-2 48 h treatment.

FIGS. 6A and 6B. HS-24 cells plated on either polylysine coated plates (non stimulated, resting) or fibronectin coated plates (stimulated) were treated with siRNA-2, or siRNA-1 (control), or piceatannol. Cells were treated with 10 ng/ml of TNF during overnight culture. (FIG. 6A) Following siRNA (48 h) or piceatannol (16 h) treatment, cells were removed, immunostained with anti-CD54 (ICAM-1) and analysed by flow cytometry. (FIG. 6B) Cell culture supernatants were analysed for IL-6 release using an IL-6 ELISA kit. *P<0.05, **P<0.005 as compared to untreated cells (e.g., untreated with siRNA) stimulated with TNF. Results are representative of three to five independent experiments. The data indicate that inhibition of Syk expression by siRNA-2 down-regulates TNF-induced ICAM-1 expression and IL-6 release, important in the inflammatory response.

(FIG. 7A provides data as bar graphs, FIG. 7B shows individual data points (individual animals).

(FIG. 8A provides data as bar graphs, FIG. 8B shows individual data points (individual animals) for macrophage numbers, FIG. 8C shows individual data points for neutrophil numbers, and FIG. 8D shows individual data points for eosinophil numbers.)

DETAILED DESCRIPTION OF THE INVENTION

Figure 2:
FIG. 2. Expression of Syk kinase in RBL-2H3 cells transfected with siRNA targeted to Syk kinase mRNA. RBL-2H3 cells were transfected with siRNA-1 (Lane 2), siRNA-2 (lane 3) or lipofectamine transfection control (Lane 1). Proteins in cell lysates were separated by SDS-PAGE and transferred to nitrocellulose. Top panel, Syk kinase immunoblot; bottom panel, actin immunoblot.
Figure 2:

The present invention relates to RNA molecules that target Syk kinase mRNA. For example, the invention relates to RNA molecules about 19, 20 or 21 to about 23 nucleotides in length that direct cleavage and/or degradation of Syk kinase mRNA.

In a preferred embodiment, the present invention relates to the use of siRNA molecules, double stranded RNA molecules typically comprising two 20–23 nucleotide (nt) strands. SiRNAs suitable for use in the invention can be produced using any of a variety of approaches. The siRNA can be prepared in vitro and then introduced directly into cells (for example, by transfection). Alternatively, intracellular expression can be effected by transfecting into cells constructs (e.g., DNA-based vectors or cassettes) that express siRNA within cells.

More specifically, siRNA suitable for use in the invention can be prepared, for example, via chemical synthesis, in vitro transcription, enzymatic digestion of a longer dsRNA using an RNase III enzyme such as Dicer or RNase III, expression in cells from an siRNA expression plasmid or viral vector, or expression in cells from a PCR-derived siRNA expression cassette. Detailed descriptions of these various approaches are readily available and can be found, for example, at http://www.ambion.com/techlib/tn/103/2.html, www.bdbiosciences.com, www.oligoengine.com, www.genetherapysystems.com, www.dharmacon.com, http://www.mpibpc.gwdg.de/abteilungen/100/105/sirna.html, and/or in the references cited therein (which references are also incorporated herein by reference). (See also Sui et al, Proc Natl Acad Sci USA 99: 5515–20 (2002), Brummelkamp et al, Science 296:550–3 (2002), Paul et al, Nature Biotechnology 20:505–8 (2002), Lee et al, Nature Biotechnology 20: 500–5 (2002), Castanotto et al, RNA 8: 1454–60 (2002) and US Appln. 20030108923.)

Various approaches are available to enhance stability of RNA of the invention, (see, for example, U.S. Application Nos. 20020086356, 20020177570 and 20020055162, and U.S. Pat. Nos. 6,197,944, 6,590,093, 6,399,307, 6,057,134, 5,939,262, and 5,256,555, and references cited therein).

As indicated above, siRNA suitable for use in the invention can be prepared chemically. Advantageously, 2' hydroxyls are protected during the synthetic process against degradation using, for example, acid labile orthoester protecting groups (see Scaringe et al, J. Am. Chem. Soc. 120:11820 (1998) and www.dharmacon.com (e.g., the ACE technology described therein)). The RNA oligomers can be simultaneously 2' deprotected and annealed prior to use.

In chemically synthesized siRNA, at least one strand of the double stranded molecule can have a 3' overhang from about 1 to about 6 nucleotides (e.g., pyrimidine and/or purine nucleotides) in length. Preferably, the 3' overhang is from about 1 to about 5 nucleotides (e.g., thymidines or uridines), more preferably from about 1 to about 4 nucleotides and most preferably 2 or 3 nucleotides in length. Advantageously, each strand has an overhang. The length of the overhangs can be the same or different for each strand. Typically, both strands have overhangs of the same length. In a particular embodiment, the RNA of the present invention comprises 21 or 22 nucleotide strands that are paired and that have overhangs of from about 1 to about 3, particularly, about 2, nucleotides on the 3' ends of both of the RNA strands.

As indicated above, siRNAs suitable for use in the invention can be prepared by enzymatic digestion of a longer dsRNA using an RNase III type enzyme (e.g., Dicer). (See references and web sites cited above.) For example, a commercially available Dicer siRNA generation kit can be used that permits generation of large numbers of siRNAs from full length target genes (Gene Therapy Systems, Inc, MV062603). SIRNA can be produced from target DNA and T7 RNA polymerase promoter sequences using PCR based cloning. Following RNA transcription from the target sequence, recombinant Dicer can cleave the transcribed RNAi into 22 bp siRNAs.

Also as indicated above, siRNA molecules suitable for use in the present invention can also be recombinantly produced using methods known in the art. (See references and web sites cited above.) Recombinant technology permits in vivo transcription of siRNAs in mammalian cells. In accordance with this approach, vectors can be used that contain, for example, RNA polymerase III or U6 promoter sequences. Such vectors (including viral vectors and plasmid vectors (such as pSIREN)) can be used as expression vectors or as shuttle vectors in conjunction with viral systems (e.g., adenoviral or retroviral systems) to introduce siRNA into mammalian cells. Vectors can be engineered to express sense and anti-sense strands of siRNAs that anneal in vivo to produce functional siRNAs. Alternatively, hairpin RNA can be expressed by inserting into a vector the sense strand (e.g., about 20 nt) of the target, followed by a short spacer (e.g., about 4 to about 10 nt), then the antisense strand of the target (e.g., about 20 nt) and, for example, about 5–6 U's as transcription terminator. The resulting RNA transcript folds back to form a stem-loop structure comprising, for example, about a 20 bp stem and about a 10 nt loop with 2–3 U's at the 3' end. (See also Paddison et al (Proc. Natl. Acad. Sci. 99:1443–1448 (2002).) Constructs suitable for use in effecting in vivo production (including selection of vectors and promoters) can be readily designed by one skilled in the art and will vary, for example, with the cell/tissue target and the effect sought.

dsRNA can be used in the methods of the present invention provided it has sufficient homology to the targeted Syk kinase mRNA. SIRNA duplexes can be designed, for example, by searching Syk kinase cDNA for the target motif "AA(N)$_{19}$", wherein N is any nucleotide, motifs with approximately 30% to 70% G/C content being preferred, those of about 50% G/C content being more preferred. The sense strand of the siRNA duplex can correspond to nucleotides 3 to 21 of the selected AA(N)$_{19}$ motif. The antisense strand of the siRNA duplex can have a sequence complementary to nucleotides 1 to 21 of the selected AA(N)$_{19}$ motif. Further design details are provided at http://www.mpibpc.gwdg.de/abteilungen/100/105/sirna.html.

Preferred target sequences include sequences unique to Syk kinase mRNA. For example, target sequences can be selected from sequences between the two SH2 domains of Syk kinase or between the second SH2 domain and the kinase domain. Certain specific DNA target sequences are described in the non-limiting Examples that follow. Additional targets include, but are not limited to, the following (SEQ ID NOS 1–22, respectively, in order of appearance):

| *Sequence | % GC | Identified homologies of 16–18/19 nucleotides |
|---|---|---|
| AATATGTGAAGCAGACATGGA | 42 | mitochondrial ribosomal prot15 |
| AATCAAATCATACTCCTTCCC | 42 | |
| AAGAGAGTACTGTGTCATTCA | 42 | |
| AAGGAAAACCTCATCAGGGAA | 47 | inositolhexaphosphate kinase, β globin on Chr11 |
| AATCATACTCCTTCCCAAAGC | 47 | |
| AATTTTGGAGGCCGTCCACAA | 53 | oxytokinase |
| AAGACTGGGCCCTTTGAGGAT | 58 | |
| AAGCAGACATGGAACCTGCAG | 58 | histamine receptor H3, GTP binding protein |
| AACTTCCAGGTTCCCATCCTG | 58 | |
| AAGCCTGGCCACAGAAAGTCC | 63 | |
| AAGCCCTACCCATGGACACAG | 63 | |
| AACCTGCAGGGTCAGGCTCTG | 68 | |
| AAGGGGTGCAGCCCAAGACTG | 68 | γ glutamyl transferase, rb prot L27a |
| AACTTGCACCCTGGGCTGCAG | 68 | calcium channel α1E subunit |
| AAGTCCTCCCCTGCCCAAGGG | 74 | NADH; ubiquinone oxidoreductase MLRQ subunit |
| AAGGCCCCAGAGAGAAGCCC | 74 | |
| AATCTCAAGAATCAAATCATA | 26 | |
| AATGTTAATTTTGGAGGCCGT | 42 | |
| AATCCGTATGAGCCAGAACTT | 47 | |
| AATCGGCACACAGGGAAATGT | 53 | |
| AACCGGCAAGAGAGTACTGTG | 58 | |
| AAGGAGGTTTACCTGGACCGA | 58 | |

The siRNAs described herein can be used in a variety of ways. For example, the siRNA molecules can be used to target Syk kinase mRNA in a cell or organism. In a specific embodiment, the siRNA can be introduced into human cells or a human in order to mediate RNAi in the cells or in cells in the individual, so as to prevent or treat a disease or undesirable condition associated with Syk kinase expression (e.g., inflammation of the lungs, joints eyes or bladder). The siRNA can also be used in the treatment of the immune destruction of blood cells, e.g., red blood cells in autoimmune hemolytic anemia and platelets in immune thrombocytopenic purpurea (ITP) (e.g., by targeting Syk kinase mRNA in macrophages and spleen and liver cells). In accordance with the instant method, the Syk kinase gene is targeted and the corresponding mRNA (the transcriptional product of the targeted Syk kinase gene) is degraded by RNAi. When lung cells are the target, an siRNA-containing composition can be aerosolized and administered, for example, via inhalation. Administration to joints can be effected by injection of an siRNA-containing solution. Administration to the eyes can be effected, for example, by injection or by application of drops comprising the siRNA in a carrier. Administration to the bladder, etc. can be effected, for example, by washing or irrigating the target tissue with a composition containing the siRNA. Administration to the skin can be via topical administration (e.g., as a liquid, cream or gel).

In accordance with the invention, cells of an individual (e.g., blood mononuclear cells, basophiles or mast cells) can be treated ex vivo so as to effect degradation of the Syk kinase mRNA. The cells to be treated can be obtained from the individual using known methods and the siRNAs that mediate degradation of the corresponding Syk kinase mRNA can be introduced into the cells, which can then be re-introduced into the individual.

In a specific embodiment, the invention relates to the use of the above-described siRNAs to inhibit mediator (e.g., histamine) release from cells bearing an Fc∈ receptor, such as mast cells. Inhibition of histamine (a mast cell mediator) release, for example, is of therapeutic importance in the treatment of asthma.

The siRNAs (or constructs suitable for use in effecting intracellular production of siRNA) of the invention can be administered systemically (e.g., via IV) or directly to the target tissue (e.g., via aerosol administration to the lung). Delivery can be effected using the techniques described herein (including liposome formulations). In addition to liposome formulations, polymer formulations can be used. Polyethylenimine (PEI) is an example of a suitable cationic polymer. Varying sizes of PEI can be used, including linear 22 kDa and branched 25 kDa PEI (other sizes, modified and unmodified, as well as biodegradable versions can be used). Delivery can also be effected using, for example, non-toxic viral delivery systems (e.g., an adeno-associated viral delivery system). Optimum dosing will depend on the patient, the siRNA, the mode of administration, and the effect sought. Optimum conditions can be established by one skilled in the art without undue experimentation.

Certain aspects of the invention can be described in greater detail in the non-limiting Examples that follows. (See also U.S. Applications 20030084471, 20030108923 and 20020086356.)

EXAMPLE 1

Experimental Details

Reagents

Lipofectamine 2000 and Opti-Mem were purchased from Invitrogen (San Diego, Calif.). Eagle's MEM (EMEM), FCS, penicillin, and streptomycin were purchased from Life Technologies (Grand Island, N.Y.). Rabbit anti-murine Syk kinase polyclonal antibodies (Ab) and anti-actin Ab were purchased from Santa Cruz Biotechnology (Santa Cruz, Calif.), and F(ab')$_2$ goat anti-rabbit Ab was supplied by The Jackson Laboratory (Bar Harbor, Me.). Chemiluminescence reagent was purchased from DuPont NEN (Boston, Mass.).

Cells and Cell Lines

Peripheral blood monocytes obtained from healthy volunteers at the University of Pennsylvania were isolated as previously described (Matsuda et al, Molec. Biol. of the Cell 7:1095–1106 (1996)). Briefly, heparinized blood was centrifuged on Ficoll-Hypaque (Lymphocyte Separation Medium; Organon Teknika, Durham, N.C.) and interface cells were resuspended in complete medium containing RPMI 1640 (GIBCO BRL, Grand Island, N.Y.), 10% heat inactivated-fetal calf serum (FCS) (Intergen, Purchase, N.Y.) and 2 mM L-glutamine. Cells were allowed to adhere at 37° C. for 30 min to tissue culture flasks precoated with FCS. After 45–90 min, nonadherent cells were removed by extensive washing in Hanks' balanced salt solution. Cells were harvested by vigorous agitation. Monocytes were routinely >98% viable as judged by Trypan Blue exclusion. Isolated monocytes were maintained in RPMI 1640 supplemented with L-glutamine (2 mM) and 10% heat inactivated FCS at 37° C. in 5% $CO_2$.

Rat basophilic cells (RBL-2H3) were grown in EMEM supplemented with 17% FBS, 100 U penicillin, 100 μg/ml streptomycin, and 4 mM glutamine at 37° C. in 5% $CO_2$.

siRNA Duplex Construction siRNAs for Syk kinase were prepared by Dharmacon Research Inc. (Lafayette, Co). In designing the siRNAs according to the guidelines provided by the manufacturer, potential siRNA targets (19 nucleotides immediately downstream of AA pairs) in human Syk kinase RNA were first identified. These sites were then scanned in the sequences of rat and mouse Syk kinase RNA in order to identify common Syk kinase RNA target sequences in these species. Two appropriate sites were identified, and two 21-mer RNAs, each consisting of 19 complementary nucleotides and 3' terminal noncomplementary dimers of thymidine (Elbashir et al, Nature 411:494–498 (2001)), were constructed. The sense strand of the siRNA is the same sequence as the target mRNA sequence with the exception of the terminal thymidine dimer. The antisense strand of the siRNA is the reverse complement of the target sequence.

1) siRNA-1: Human, bp 296 to bp 316; Mouse and Rat, bp 307 to bp 327.

```
                                         (SEQ ID NO: 23)
sense      5' gaagcccuucaaccggccc UU 3'

(SEQ ID NO: 24)
antisense  3'-UU cuucgggaaguuggccggg 5'
```

2) siRNA-2: Human, bp 364 to bp 382; Mouse and Rat, bp 375 to bp 393

```
                                         (SEQ ID NO: 25)
sense      5'-ccucaucagggaauaucug UU 3'

(SEQ ID NO: 26)
antisense  3'-UU ggaguaguccccuuauagac 5'
```

Transfections

SIRNA was introduced into RBL-2H3 cells and into monocytes by transfection. For the transfections, $5 \times 10^4$ RBL-2H3 cells or $1 \times 10^5$ monocytes were seeded into each well of a 24-well plate. Twenty-four hours later, the complete medium was replaced with 400 μl fresh medium lacking serum and antibiotic and siRNA/Lipofectamine 2000 complex was added to each well. For the RBL cells, the siRNA/Lipofectamine 2000 complex was formed by adding 3 μl of siRNA duplex (20 μM) and 3 μl of Lipofectamine 2000 to 100 μl Opti-mem without serum or antibiotic according to the manufacturer's protocol. For monocytes, the siRNA/Lipofectamine 2000 complex was formed by adding 3 μl of siRNA duplex (20 μM) and 1 μl of Lipofectamine 2000 to 100 μl Opti-mem without serum or antibiotic. Cells were incubated at 37° C. for 48 hours before examination of kinase protein expression by Western blotting Western Blot Analysis of Syk Kinase Protein Lysates were prepared by boiling cells in Laemmli sample buffer (2% SDS, 10% glycerol, 100 mM DTT, and 60 mM Tris (pH 6.8) for 5 minutes. Proteins in lysates were separated by SDS-PAGE (10% polyacrylamide) and transferred to a nitrocellulose membrane in sample buffer (25 mM Tris, 190 mM glycine, and 20% methanol). The nitrocellulose membrane was incubated overnight at 4° C. with 1 μg/ml rabbit anti-murine Syk kinsae polyclonal Ab before incubation with goat anti-rabbit HRP (1.5 h at room temperature). Protein bands on the membrane were visualized with chemiluminescence reagent according to the manufacturer's protocol. After detection of Syk kinase protein, the anti-Syk kinase Ab was removed by incubating the membrane in a stripping buffer containing 100 mM 2-ME, 2% SDS, and 62.5 mM Tris-HCL (pH 6.7) for 30 minutes at 50° C. with occasional agitation. The membrane was then reprobed with anti-actin Ab and bands on the membrane were visualized with chemiluminescence reagent. Protein levels of Syk kinase were quantified by densitometry (Personal Densitometer, Molecular Dynamics).

Results

Effects of siRNA on the Expression of Syk Kinase

Figure 3:
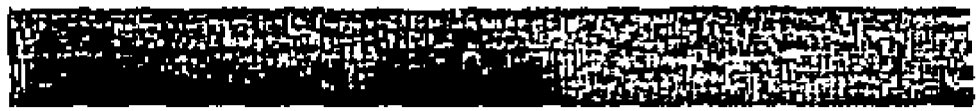
FIG. 3. Expression of Syk kinase in human monocytes transfected with siRNA targeted to Syk kinase mRNA. Monocytes were treated with siRNA (Lane 2) or lipofectamine transfection control (Lane 1). Proteins in cell lysates were separated by SDS-PAGE, transferred to nitrocellulose and immunoblotted with anti-Syk kinase antibody.

Rat basophilic cells (RBL-2H3 cells) and human monocytes were transfected with siRNA directed to sequences common to rat, mouse and human Syk kinase RNA. The expression of Syk kinase protein was analyzed by Western blotting using anti-Syk kinase Ab (FIGS. 2 and 3). Inhibition of Syk kinase expression in RBL cells treated with siRNA is shown in FIG. 2, and levels of Syk kinase protein, normalized to levels of actin protein, are presented in Table 1. Actin is a common protein used as a standard to examine protein expression. Syk kinase protein expression in siRNA-treated RBL cells was inhibited by 45–51% (FIG. 2, lanes 2 and 3) compared to untreated RBL cells (lane 1). The magnitude of the inhibition of Syk kinase gene expression by siRNA in cultured cells was encouraging since previous experiments with Syk kinase mRNA ASO indicated that greater levels of Syk kinase inhibition can be achieved in non-multiplying cells such as monocytes than in multiplying cells cultured in vitro. Inhibition of Syk kinase expression by siRNA in monocytes maintained in culture (FIG. 3) was also observed. Syk kinase expression in siRNA-treated monocytes was inhibited (FIG. 3, lane 2). In addition, Syk kinase expression in siRNA-treated U937 cells and siRNA-treated THP-1 cells was inhibited (U937 and THP-1 being macrophage-like cell lines). The data thus demonstrate the effectiveness of siRNA directed against Syk kinase RNA to suppress the expression of this gene and indicate that siRNA directed against Syk kinase RNA can serve as a powerful therapeutic tool to combat inflammation.

TABLE 1

Densitometry quantification of Syk kinase expression in RBL cells.

|  | Transfection Control | Syk kinase siRNA1 | Syk kinase siRNA2 |
| --- | --- | --- | --- |
| Syk* | 2040 | 953 | 627 |
| Syk Corr** | — | 1114 | 997 |
| % Syk Inhibition | 0 | 45 | 51 |

*densitometry units
**Syk densitometry units corrected for % actin expression in each lane.

Discussion

The siRNAs used in these studies were chemically synthesized (Dharmicon Research Inc., Lafayette, Colo.) but siRNAs can also be prepared by recombinant techniques. siRNA duplexes can comprise 21-nucleotide sense and 21-nucleotide antisense strands, paired in a manner to have a 2-nucleotide (dT) 3' overhang.

The targeted region for siRNAs can be the sequence AA(N19) (N, any nucleotide) selected from the designated cDNA sequence beginning 50 to 100 nucleotides downstream of the start codon. G/C-contents of approximately 50% are preferred. Since expression of RNAs from pol III promoters is only efficient when the first transcribed nucleotide is a purine, it is preferred that the sense and antisense siRNAs begin with a purine nucleotide so that they can be expressed from pol III expression vectors without a change in targeting site.

In the studies described above, potential siRNA targets in human Syk kinase mRNA were selected and then the sequences in rat and mouse Syk kinase imRNA were scanned in order to identify common Syk kinase mRNA target sequences in these species. Two appropriate target sequences were identified:

```
Targeted region (1) (cDNA):
5'aagaagcccttcaaccggccc;        (SEQ ID NO: 27)

Targeted region (2) (cDNA):
5'aacctcatcagggaatatgtg.        (SEQ ID NO: 28)
```

The target sequences and Syk kinase siRNAs are shown in FIG. 1. Duplexed RNA is not highly susceptible to nuclease degradation and the use of deoxynucleotides (thymidine (T) rather than uridine (U)) may affect the stability of the 3' overhang.

EXAMPLE 2

HS-24 cells ($2\times10^5$) were pre-treated with 3 µl of siRNA-1 (control)

```
                                       (SEQ ID NO: 27)
DNA Target:    5' AAGAAGCCCTTCAACCGGCCC (SEQ ID NO: 23)
Sense siRINA   5' gaagcccuucaaccggccc UU 3'

(SEQ ID NO: 24)
Antisense siRNA  3'-UU cuucgggaaguuggccggg 5' or siRNA-2

(SEQ ID NO: 28)
DNA Target:    5' AACCTCATCAGGGAATATCTG (SEQ ID NO: 25)
Sense          5'- ccucaucagggaauaucug UU 3'

(SEQ ID NO: 26)
antisense      3'-UU ggaguagucccuuauagac 5'
``` or Syk antisense, with Lipofectamine 2000 in a 12-well plate for 24 or 48 hr, and stimulated by 10 ng/ml of TNF overnight. Read-outs: IL-6 in culture supernatant (ELISA) and cell surface expression of ICAM-1 (Flow cytometry). As shown by Western blot analysis (see FIG. 4), siRNA-2 caused a decrease in Syk protein expression following 48 hr of treatment.

More specifically, HS-24 cells were transiently transfected with siRNA-2 or siRNA-1 (control). Cell surface expression of ICAM-1, as well as release of IL-6, were then examined. Forty-eight-hour treatment of HS-24 cells with siRNA-2, but not with siRNA-1, significantly suppressed both Syk protein (FIG. 5A) and mRNA (FIG. 5B) expression.

HS-24 cells constitutively expressed low levels of ICAM-1 (FIG. 6A) not affected by siRNA-2 treatment (not shown). Stimulation of HS-24 cells with 10 ng/ml of TNF during overnight culture caused significant increase in ICAM-1 expression both in resting cells (plated on poly-L-lysine) and cells adherent to fibronectin (FIG. 6A). Cells adherent to fibronectin showed higher expression of ICAM-1 following stimulation with TNF compared to cells adherent to poly-L-lysine (P<0.05). Transfection with siRNA-2 down-regulated TNF-induced ICAM-1 expression in fibronectin-plated HS-24 cells (P<0.005), but had no significant effect on ICAM-1 in poly-L-lysine-plated cells. Overnight treatment with the pharmacological Syk inhibitor, piceatannol (10 µM), caused significant down-regulation of ICAM-1 in TNF-stimulated cells both in poly-L-lysine and fibronectin adherent conditions (FIG. 6A). As determined by trypan blue dye exclusion, the treatment of cells with siRNA or piceatannol had no significant effect on viability (in all experiments, viability was >96%).

Although IL-6 release by HS-24 cells without TNF stimulation was minimal, there was a trend to higher IL-6 levels in culture supernatants of cells adherent to fibronectin (FIG. 6B). As expected, a great elevation of IL-6 levels was observed following TNF stimulation in both culture conditions, with higher levels in fibronectin-adherent cells (P<0.05). SiRNA-2 treatment caused down-regulation of IL-6 release (55–58%) that reached statistical significance in fibronectin-adherent culture (P<0.05). Piceatannol almost completely inhibited TNF-induced IL-6 release (FIG. 6B).

Thus, inhibition of Syk kinase down-regulated TNF-induced expression of ICAM-1 and IL-6 release, hallmarks of inflammatory responses in the airway epithelium. The effect was significant in cells adherent to fibronectin indicating that Syk involvement in these pro-inflammatory events is at least partly β1 integrin dependent.

EXAMPLE 3

The effects of siRNA targeted to Syk kinase was studied in vivo in a Brown Norway rat model of ovalbumin (OA)-induced asthma.

Brown Norway rats were sensitized to OA i.p. as described (Laberge et al, Am. J. Respir. Crit. Care Med. 151:822 (1995)) and used on day 21 following sensitization.

The siRNA used in this Example is as follows:

```
                                       (SEQ ID NO: 28)
DNA Target: 5' AACCTCATCAGGGAATATCTG (SEQ ID NO: 29)
Sense       5'- ccucaucagggaauaucug uu 3'

(SEQ ID NO: 30)
antisense   3'-uu ggaguagucccuuauagac 5'
```

Figure 7A:
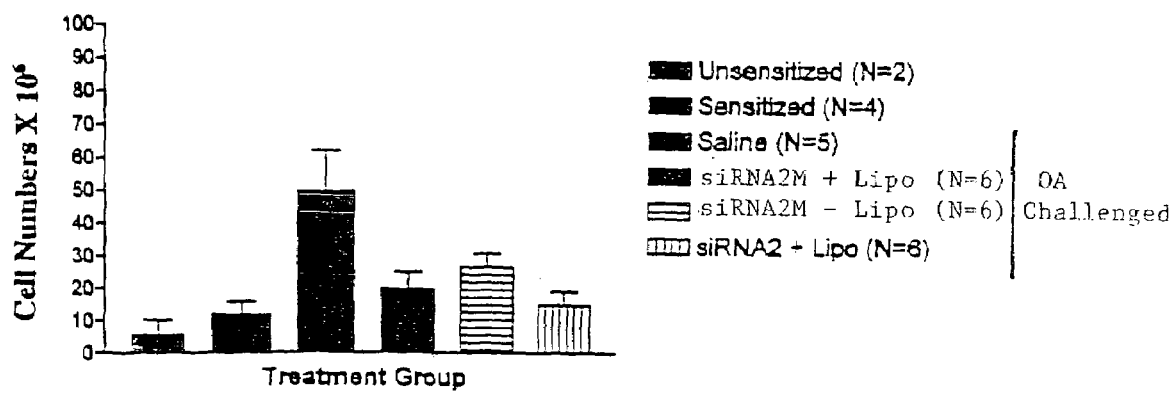
FIGS. 7A and 7B. Effect of siRNA targeted to Syk kinase delivered via aerosol on total cell numbers in bronchoalveolar lavage (BAL) fluid of ovalbumin (OA) sensitized and challenged Brown Norway Rats after three treatments.
Figure 7B:
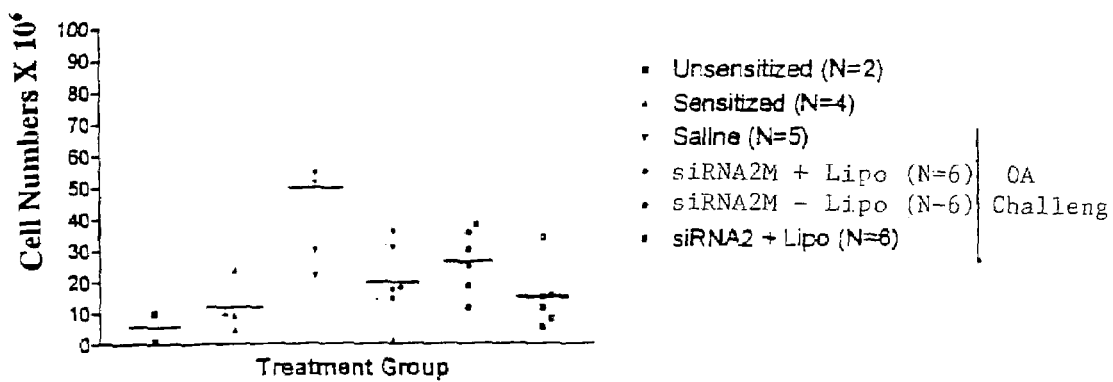
Figure 8A:
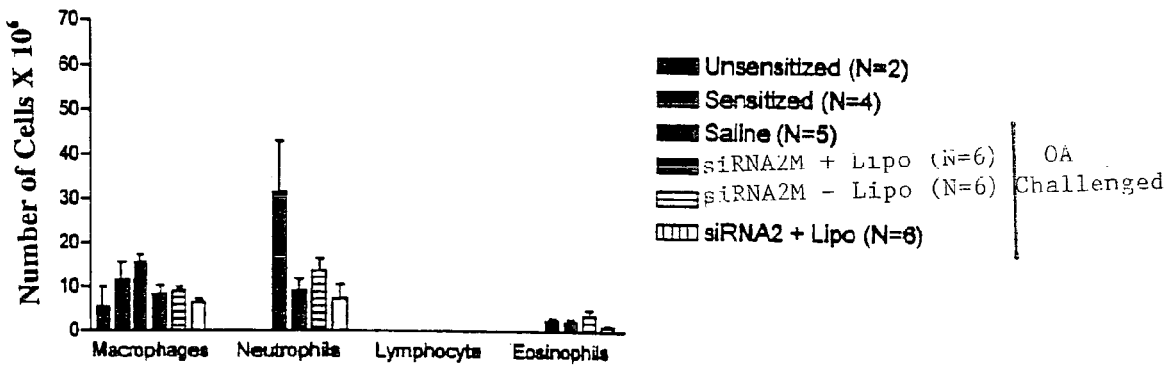
FIGS. 8A–8D. Effect of siRNA targeted to Syk kinase delivered via aerosol on numbers of macrophages, neutrophils, lymphocytes and eosinophils in BAL fluid of OA sensitized and challenged Brown Norway rats after three treatments.
Figure 8B:
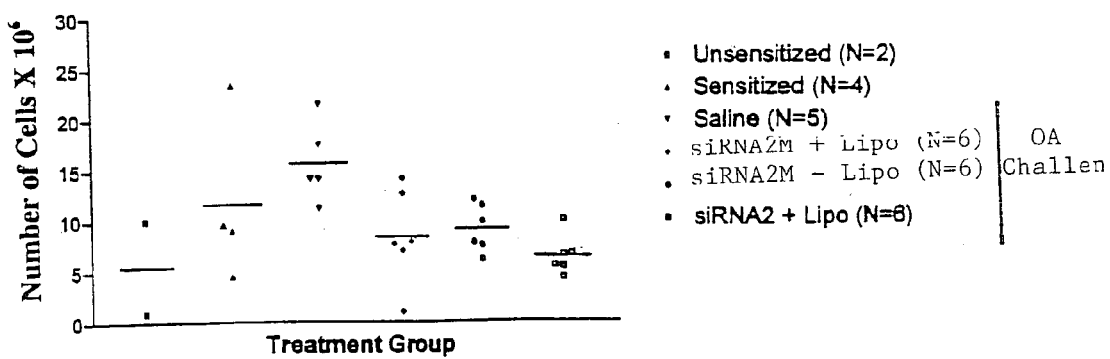
Figure 8C:
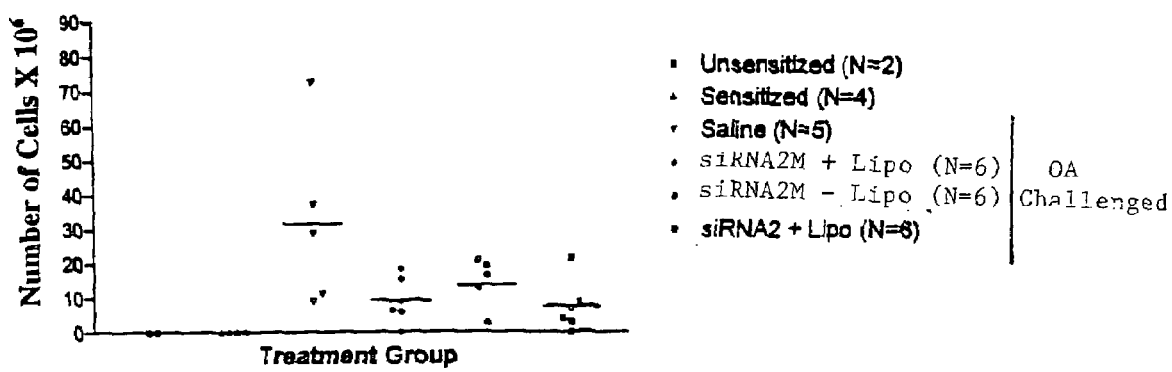
Figure 8D:
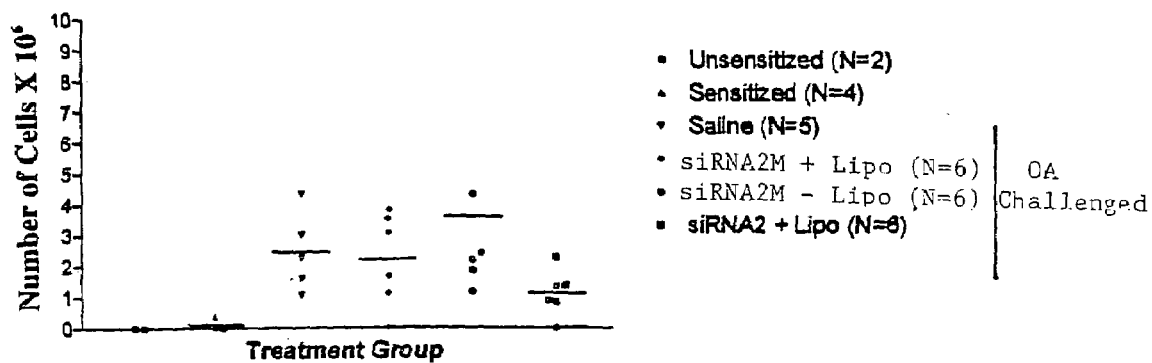

The description siRNA 2M, used in FIGS. 7 and 8, refers to the above, modified by Dharmacon to provide additional stability. The designation siRNA-2, used in FIGS. 7 and 8, refers to the above sequence in unmodified form.

SiRNA was used alone without liposome or was used after formation of siRNA/liposome complexes. 1,2 Dioleoyl-3-trimethylammonium-propane (DOTAP)/dioleoylphosphatidyl-ethanol-amine (DOPE) liposomes were prepared as previously described (see Stenton et al, J. Immunol. 169:1028 (2002) and references cited therein). Cationic DOTAP:DOPE liposomes were incubated at a 2.5:1 ratio of the liposome to the siRNA and 125 micrograms of siRNA (with or without liposomes) was administered by aerosol following nebulization.

The aerosolized administration of Syk kinase-targeted siRNA was as described by Stenton et al, J. Immunol. 164:3790 (2000). Nine milliters of saline, siRNA or siRNA/liposome were administered per rat by nebulization for 45 min using a Sidestream nebulizer as described in Stenton et al, J. Immunol. 169:1028 (2002). Twenty-four hours later, the procedure was repeated, followed by a third treatment at 48 h. Immediately after the third treatment, rats were challenged with aerosolized saline or 5% OA in saline for 5 min. Twenty-four hours after challenge, the animals were sacrificed.

Bronchoalveolar lavage (BAL) was carried out as described by Stenton et al, J. Immunol. 169:1028 (2002).

The isolated BAL cells were counted and cell smears were prepared by Cytospin. Cell differentials were counted in a blinded fashion following staining with HEMA-3 reagent (Biochemical Sciences, Swedesboro, N.J.).

Summarizing, the Brown Norway rat model of OA induced allergic asthma and pulmonary inflammation was used in the above-described studies. Pulmonary inflammation, as determined by recruitment of cells to BAL fluid, was dramatically inhibited by Syk kinase-targeted siRNA in the presence and absence of liposomes.

All documents and other information sources cited above are hereby incorporated in their entirety by reference.

SEQUENCE LISTING

```
<160> NUMBER OF SEQ ID NOS: 30

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
aatatgtgaa gcagacatgg a                                                 21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
aatcaaatca tactccttcc c                                                 21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
aagagagtac tgtgtcattc a                                                 21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
aaggaaaacc tcatcaggga a                                                 21
```

```
<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
aatcatactc cttcccaaag c                                            21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
aattttggag gccgtccaca a                                            21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
aagactgggc cctttgagga t                                            21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
aagcagacat ggaacctgca g                                            21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
aacttccagg ttcccatcct g                                            21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
aagcctggcc acagaaagtc c                                            21
```

```
<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
aagccctacc catggacaca g                                          21

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
aacctgcagg gtcaggctct g                                          21

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13 aagggggtgca gcccaagact g                                         21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
aacttgcacc ctgggctgca g                                          21

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
aagtcctccc ctgcccaagg g                                          21

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
aaggccccca gagagaagcc c                                          21
```

```
<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
aatctcaaga atcaaatcat a                                              21

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
aatgttaatt ttggaggccg t                                              21

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
aatccgtatg agccagaact t                                              21

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
aatcggcaca cagggaaatg t                                              21

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
aaccggcaag agagtactgt g                                              21

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
aaggaggttt acctggaccg a                                              21

<210> SEQ ID NO 23
```

```
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 23
gaagcccuuc aaccggccct t                                           21

<210> SEQ ID NO 24
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 24
gggccgguug aagggcuuct t                                           21

<210> SEQ ID NO 25
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 25
ccucaucagg gaauaucugt t                                           21

<210> SEQ ID NO 26
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 26
cagauauucc cugaugaggt t                                           21

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
aagaagccct tcaaccggcc c                                           21

<210> SEQ ID NO 28
<211> LENGTH: 21
<212> TYPE: DNA
```

-continued

```
<213> ORGANISM: Artificial Sequence
<220> FEATURE:
<223> OTHER INFORMATION: Description of Artificial Sequence: Synthetic
      oligonucleotide

<400> SEQUENCE: 28
aacctcatca gggaatatct g                                               21

<210> SEQ ID NO 29
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
ccucaucagg gaauaucugu u                                               21

<210> SEQ ID NO 30
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
cagauauucc cugaugaggu u                                               21
```

What is claimed is:

1. A method of inhibiting expression of Syk kinase in a patient comprising administering to said patient small interfering RNA (siRNA) molecules that direct cleavage of a target Syk kinase mRNA sequence present in said patient thereby effecting said inhibition.

2. The method according to claim 1 wherein said siRNA molecules are about 20–23 nucleotides in length.

3. The method according to claim 1 wherein said siRNA molecules are introduced directly into said patient.

4. The method according to claim 1 wherein said siRNA molecules are produced intracellularly following introduction into said patient of a nucleotide sequence encoding said siRNA molecule.

5. The method according to claim 1 wherein said siRNA molecules comprise two strands, and at least 1 strand of said siRNA molecules has a 3' overhang of about 1 to about 6 nucleotides in length.

6. The method according to claim 5 wherein both strands of said siRNA molecules have 3' overhangs of about 2 to 3 nucleotides in length.

7. The method according to claim 6 wherein said 3' overhangs comprise uridines or thymidines.

8. The method according to claim 1 wherein said target sequence comprises a nucleotide sequence selected from the group consisting of (SEQ ID NOS 1–22 & 28, respectively, in order of appearance (wherein said nucleotide sequence is presented as a cDNA)):

AATATGTGAAGCAGACATGGA,

AATCAAATCATACTCCTTCCC,

-continued

AAGAGAGTACTGTGTCATTCA,

AAGGAAAACCTCATCAGGGAA,

AATCATACTCCTTCCCAAAGC,

AATTTTGGAGGCCGTCCACAA,

AAGACTGGGCCCTTTGAGGAT,

AAGCAGACATGGAACCTGCAG,

AACTTCCAGGTTCCCATCCTG,

AAGCCTGGCCACAGAAAGTCC,

AAGCCCTACCCATGGACACAG,

AACCTGCAGGGTCAGGCTCTG,

AAGGGGTGCAGCCCAAGACTG,

AACTTGCACCCTGGGCTGCAG,

AAGTCCTCCCCTGCCCAAGGG,

AAGGCCCCAGAGAGAAGCCC,

AATCTCAAGAATCAAATCATA,

AATGTTAATTTTGGAGGCCGT,

AATCCGTATGAGCCAGAACTT,

AATCGGCACACAGGGAAATGT,

AACCGGCAAGAGAGTACTGTG,

-continued

AAGGAGGTTTACCTGGACCGA, and

AACCTCATCAGGGAATATCTG.

9. The method according to claim 1 wherein said patient is a human.

10. The method according to claim 9 wherein said human is a patient suffering from an inflammatory condition and said siRNA molecules are administered in an amount sufficient to effect treatment of said condition.

11. The method according to claim 10 wherein said inflammatory condition is a condition of the bronchi, lungs, eyes, bladder or skin of said patient.

12. The method according to claim 11 wherein said inflammatory condition is a condition of the bronchi or lungs and said siRNA molecules are introduced into bronchi or lung cells by inhalation.

13. The method according to claim 1 wherein said siRNA molecules are not present in a liposome.

14. The method according to claim 1 wherein said target sequence is a sequence unique to Syk kinase mRNA.

* * * * *